(12) United States Patent
Gerber

(10) Patent No.: US 7,879,333 B2
(45) Date of Patent: Feb. 1, 2011

(54) METHODS FOR PREPARING AND DELIVERING ADJUVANT COMPOSITIONS

(75) Inventor: Jay D. Gerber, Omaha, NE (US)

(73) Assignee: Advanced BioAdjuvants, LLC, Omaha, NE (US)

( * ) Notice: Subject to any disclaimer, the term of this patent is extended or adjusted under 35 U.S.C. 154(b) by 0 days.

(21) Appl. No.: 10/792,725

(22) Filed: Mar. 5, 2004

(65) Prior Publication Data

US 2004/0170640 A1 Sep. 2, 2004

Related U.S. Application Data

(62) Division of application No. 10/426,654, filed on May 1, 2003, now abandoned, which is a division of application No. 09/884,201, filed on Jun. 19, 2001, now Pat. No. 6,676,958.

(51) Int. Cl.
*A61K 39/00* (2006.01)
*A61K 9/00* (2006.01)
*A61K 9/14* (2006.01)

(52) U.S. Cl. .............. 424/184.1; 424/400; 424/484

(58) Field of Classification Search ............... 424/184.1, 424/400, 484, 439, 489, 450, 434, 435, 191.1
See application file for complete search history.

(56) References Cited

U.S. PATENT DOCUMENTS

| | | | |
|---|---|---|---|
| 4,199,561 A | | 4/1980 | Roth et al. |
| 4,708,924 A | * | 11/1987 | Nagai et al. ............... 430/110.2 |
| 4,740,365 A | | 4/1988 | Yukimatsu et al. |
| 4,832,958 A | | 5/1989 | Baudier et al. |
| 4,917,892 A | | 4/1990 | Speaker et al. |
| 4,944,942 A | | 7/1990 | Brown et al. |
| 5,026,543 A | | 6/1991 | Rijke |
| 5,084,269 A | | 1/1992 | Kullenberg |
| 5,091,188 A | | 2/1992 | Haynes |
| 5,132,117 A | | 7/1992 | Speaker et al. |
| 5,340,588 A | | 8/1994 | Domb |
| 5,352,448 A | | 10/1994 | Bowersock et al. |
| 5,451,411 A | | 9/1995 | Gombotz et al. |
| 5,500,161 A | | 3/1996 | Andrianov et al. |
| 5,550,177 A | | 8/1996 | Fanta et al. |
| 5,565,209 A | | 10/1996 | Rijke |
| 5,567,433 A | | 10/1996 | Collins |
| 5,674,495 A | | 10/1997 | Bowersock |
| 5,690,942 A | | 11/1997 | Hjorth |
| 5,716,637 A | * | 2/1998 | Anselem et al. ............. 424/450 |
| 5,811,128 A | | 9/1998 | Tice et al. |
| 5,912,000 A | | 6/1999 | Podolski et al. |
| 5,935,599 A | | 8/1999 | Dadey |
| 6,015,576 A | | 1/2000 | See et al. |
| 6,497,883 B1 | | 12/2002 | Bublot et al. |
| 6,676,958 B2 | | 1/2004 | Gerber |

FOREIGN PATENT DOCUMENTS

| | | |
|---|---|---|
| EP | 1023904 | 8/2000 |
| EP | 1097721 | 5/2003 |
| WO | WO 93/24147 | 12/1993 |

OTHER PUBLICATIONS

Gonen, Food Additives, published on www.gaianaturopathic.com (Oct. 16, 2007), pp. 1-5.*
MedlinePlus, Medical Encyclopedia, at http://www.nlm.nih.gov/MEDLINEPLUS/ency/article/002224.htm copyright 1997-2008, updated Jul. 19, 2007, p. 1.*
Hilgers et al; "Alkyl-polyacrylate esters are strong mucosal adjuvants"; Vaccine, Butterworth Scientific Guilford; Aug. 2000; pp. 3319-3325; vol. 18, No. 28; XP004205875.
6,676,958 Non Final Rejection Jan. 27, 2003.
6,676,958 Final Rejection Jun. 24, 2003.
U.S. Appl. No. 10/426,654 Non Final Rejection Aug. 19, 2004.
U.S. Appl. No. 10/426,654 Non Final Rejection Oct. 1, 2004.
U.S. Appl. No. 10/426,654 Final Rejection Mar. 24, 2005.
U.S. Appl. No. 10/426,654 Advisory Action Sep. 26, 2005.
U.S. Appl. No. 10/426,654 BPAI Decision Sep. 7, 2007.
U.S. Appl. No. 10/431,566 Non Final Rejection Mar. 9, 2004.
U.S. Appl. No. 10/431,566 Final Rejection Oct. 29, 2004.
Artursson et al. 1984 "Characterization of polyacryl starch microparticles as carriers for proteins and drugs" Journal of Pharmaceutical Sciences 73(11): 1507-1513.
Davies et al. 1992 "Evaluation of mucoadhesive polymers in ocular drug delivery. 11. Polymer-coated vesicles" Pharmaceutical Research 9(9): 1137-1144.
Sturesson and Wikingsson 2000 "Comparison of poly(acryl starch) and poly(lactide-co-glycolide) microspheres as drug delivery system for a rotavirus vaccine" Journal of Controlled Release 68(3): 441-450.

* cited by examiner

*Primary Examiner*—Blessing M Fubara
(74) *Attorney, Agent, or Firm*—Swanson & Bratschun, LLC

(57) ABSTRACT

Methods are provided for preparing and delivering an adjuvant for vaccines including lecithin and a polymer. The polymer is preferably polyacrylic acid-based. The method of preparation includes hydrating lecithin and a polymer in saline or water and mixing the lecithin and polymer to form the adjuvant.

13 Claims, No Drawings

METHODS FOR PREPARING AND DELIVERING ADJUVANT COMPOSITIONS

CROSS REFERENCE TO RELATED APPLICATION

This application is a divisional of application Ser. No. 10/426,654 filed on May 1, 2003, now abandoned which is a divisional of application Ser. No. 09/884,201, filed Jun. 19, 2001, now U.S. Pat. No. 6,676,958 which issued on Jan. 13, 2004.

FIELD OF THE INVENTION

The present invention pertains to methods for preparing and delivering vaccine onto mucosal surfaces by, for example, oral or intranasal administration or with an antigen, topically or parenterally as an injectable.

BACKGROUND OF THE INVENTION

Mucosal delivery of vaccines has been underutilized because of the problems associated with effectively delivering the vaccine antigens to the mucosal surface and to the underlying mucosal lymphoid tissue. Since mucosal surfaces are the port of entry of the majority of the infectious agents (Sabin, A. B., Vaccination at the portal of entry of infectious agents. Dev Biol Stand 33:3-9, 1976) it is important to the health of an animal to have developed a strong protective antibody and cell-mediated immune response at the portal of entry. This is best done with an adjuvant and delivery system that targets vaccine antigens to either the mucous membranes of the oral cavity, gut, nose, rectum, or vagina. Because this is not commonly done with an injectable vaccine, it would be advantageous to have a vaccine adjuvant delivery composition that would adsorb the vaccine onto the mucosal surface, and then, following absorption, be brought in contact with mucosal-associated lymphoid tissue.

For example, oral administration of a vaccine against a gut pathogen may engender a stronger immune response against such pathogens by eliciting the production of secretory immunoglobulin A antibodies at the mucosal site. This happens when the vaccine is presented to the gut-associated lymphoid tissue (O'Hagen, D, Oral Delivery of Vaccines: Formulation and Clinical Pharmacokinetic Considerations 1992, Clin. Pharmacokinet. 22 (1): 1-10). Likewise, administration of vaccine against an upper respiratory pathogen may be most effective if delivered to the mucosal-associated lymphoid tissue in the oral cavity or nasal passages. Interestingly, administration of antigens induces a mucosal immune response not only at the site of antigen application, for example the oral mucosa, but also at other mucosal sites such as the nasal mucosal (Mestecky, J I, The Common Mucosal Immune System and Current Strategies for Induction of Immune Responses in External Secretions. J Clin Immunol. 7 (4): 265-76).

Vaccinating large numbers of animals, such as cattle, swine and poultry, is extremely labor intensive and expensive. Each individual animal has to be handled at the time of vaccination in order to inject the animal with the vaccine. Most often the vaccine must be administered to the animal at least twice, and sometimes three or more times. It would be advantageous in terms of time and expense if the vaccine could be administered, simultaneously, with feed or water to a large number of animals.

Another advantage of targeting the vaccine to mucosal surfaces is that the vaccine can stimulate a protective immune response in the presence of circulating antibody that interferes with parenterally injected vaccines (Periwal, S B, et. al., Orally administered microencapsulated reovirus can bypass suckled, neutralizing maternal antibody that inhibits active immunization of neonates. J Virol 1997 (April 71(4): 2844-50).

Adjuvant systems to enhance an animal's immune response to a vaccine antigen are well known in the art. Likewise, systems for the delivery of vaccine and drugs to mucosal surfaces are known in the art. Different methods have been described to protect the vaccine antigen and drugs from degradation by stomach acid and digestive enzymes and to adsorb the antigen to the mucosal surface. Often these adjuvants and delivery systems include mixing the antigen with one or more components.

Examples of prior art adjuvants include the following.

U.S. Pat. No. 4,917,892, Speaker et al, issued Apr. 17, 1990, describes a topical delivery system comprising a viscous carrier containing a dissolved or dispersed active agent and active agent microencapsulated within a semi permeable anisotropic salt film which is the emulsion reaction product of a) a partially lipophilic, partially hydrophilic, polyfunctional Lewis acid or salt thereof in aqueous medium, such as carboxymethylcellulose, an alkali metal salt of polyacrylic acid or cross linked polyacrylic acid/polyoxyethylene, with b) a Lewis base or salt thereof in a water-immiscible, slightly polar organic solvent for the base, such as benzalkonium chloride, and piperidine. U.S. Pat. No. 5,132,117, Speaker et al., issued Jul. 21, 1992, discloses a microcapsule with an aqueous core, capsular, ionic stabilized anisotropic Lewis salt membrane formed from the interfacial reaction product of an emulsion of an aqueous solution of a water-soluble, hydrophilic polymeric Lewis acid or salt thereof with a non-aqueous solution of a lipophilic Lewis base or salt thereof. The Lewis base may be stearylamine, piperidine, or benzalkonium chloride and the Lewis acid may be carboxymethylcellulose, polyacrylic acid, or polyacrylic acid/polyoxyethylene copolymer, for example.

U.S. Pat. No. 4,740,365, Yukimatsu et al., issued Apr. 26, 1988 describes a sustained-release preparation applicable to mucous membranes in the oral cavity. The preparation consists of an active ingredient in a mixture of a polymer component (A) comprising one or more polymers selected from polyvinylpyrrolidone, polyvinyl alcohol, polyethylene glycol, alginic acid or a salt thereof, and an alternating copolymer of maleic anhydride and methyl vinyl ether and a polymer component (B) comprising one or more polymers selected from polyacrylic acid and a salt thereof. Polymer component (A) and (B) are in a ratio of 95:5 to 5:95 by weight. The preparation is layered with the active ingredient and may have optional conventional carriers and additives.

U.S. Pat. No. 5,451,411, Gombotz et al., issued Sep. 19, 1995, describes a delivery system for a cationic therapeutic agent whereupon alginate has been cross-linked in the presence of the therapeutic agent and polyacrylic acid to obtain a sustained release composition for oral delivery.

U.S. Pat. No. 5,352,448, Bowersock et al., issued Oct. 4, 1994, describes an oral vaccine formulation comprising an enzymatically degradable antigen in a hydrogel matrix for stimulation of an immune response in gut-associated lymphoid tissues. The hydrogel pellets are preferably synthesized by polymerizing methacrylic acid, in the presence of methylene bis-acrylamide and ammonium persulfate and sodium bisulfite.

U.S. Pat. No. 5,674,495, Bowersock et al., issued Oct. 7, 1997, describes a vaccine composition for oral administration comprising an alginate gel in the form of discrete particles.

The alginate gel may contain a polymer coating such a poly-l-lysine to enhance stability and to add a positive charge to the surface.

U.S. Pat. No. 4,944,942, Brown et al., issued Jul. 31, 1990, describes an intranasal vaccine for horses, which may comprise polyacrylic acid cross linked polyallyl sucrose, sold as Carbopol 934P, combined with polyoxyethylene sorbitan mono-oleate and sorbitan monolaurate, preferably at 7.5 to 15 volume percent based on the total volume of the formulation, as an adjuvant.

U.S. Pat. No. 5,500,161, Andrianov et al., issued Mar. 19, 1996, describes a method for the preparation of microparticles, and the product thereof, that includes dispersing a substantially water insoluble non-ionic or ionic polymer in a aqueous solution in which the substance to be delivered is also dissolved, dispersed or suspended, and then coagulating the polymer together with the substance by impact forces to form a microparticle. Alternatively, the microparticle is formed by coagulation of an aqueous polymeric dispersion through the use of electrolytes, pH changes, organic solvents in low concentrations, or temperature changes to form polymer matrices encapsulating biological materials.

U.S. Pat. No. 6,015,576, See et al., issued Jan. 18, 2000, describes a method that comprises orally administering lyophilized multilamellar liposomes containing the antigen wherein the liposome preparation is contained in a pill form or within an enterically coated capsule. Such an enteric coating may be composed of acrylic polymers and copolymers.

U.S. Pat. No. 5,811,128, Tice et al., issued Sep. 22, 1998, describes a method, and compositions for delivering a bioactive agent to an animal entailing the steps of encapsulating effective amounts of the agent in a biocompatible excipient to form microcapsules having a size less than approximately ten micrometers and administering effective amounts of the microcapsules to the animal. A pulsatile response is obtained, as well as mucosal and systemic immunity. The biocompatible excipient is selected from the group consisting of poly (DL-lactide-co-glycolide), poly (lactide), poly (glycolide), copolyoxalates, polycaprolactone, polyorthoesters and poly (beta-hydroxybutyric acid), polyanhydrides and mixtures thereof.

U.S. Pat. No. 5,565,209, Rijke, issued Oct. 15, 1996, describes oil-free vaccines comprising polyoxypropylene-polyoxyethylene polyols and an acrylic acid polymer as adjuvant constituents for injectable vaccines.

U.S. Pat. No. 5,084,269, Kullenberg, issued Jan. 28, 1992, describes an adjuvant, comprised of lecithin in combination with a carrier which may be selected from the group consisting of non-edible oil such as mineral oil and edible triglyceride oils such as soybean oil, for an injectable vaccine.

U.S. Pat. No. 5,026,543, Rijke, issued Jun. 25, 1991, discloses oil-free vaccines which contain polyoxypropylene-polyoxyethylene polyols as well as an acrylic acid polymer as adjuvanting constituents.

U.S. Pat. No. 5,451,411, Gombotz et al, issued Sep. 19, 1995, discloses alginate beads as a site specific oral delivery system for cationic therapeutic agents designed to target the agents to the luminal side of the small intestine. Enhanced bioactivity of therapeutic agents released from the alginate is attributed to the ability of polyacrylic acid to shield the agents from interaction with lower molecular weight fragments of acid treated alginate.

U.S. Pat. No. 5,567,433, Collins, issued Oct. 22, 1996, discloses a method of producing liposomes useful for encapsulating and delivering a wide variety of biologically active materials. The method involves the formation of a liposome dispersion in the absence of an organic solvent or detergent, one or several cycles of freezing and thawing, and dehydration to form a lipid powder. The powder is hydrated in the presence of a biologically active material to encapsulate it in the liposomes.

U.S. Pat. No. 5,091,188, Haynes, issued Feb. 25, 1992, discloses water-insoluble drugs are rendered injectable by formulation as aqueous suspensions of phospholipid-coated microcrystals.

SUMMARY OF THE INVENTION

The present invention concerns an adjuvant composition that includes lecithin and a polymer that is preferably an acrylic polymer or copolymer. The preferred acrylic polymer is a polyacrylic acid polymer.

The lecithin and polymer form a matrix or net-like structure which is effective in trapping or encapsulating vaccine antigen. Further, the strong mucoadhesive and adsorptive properties of the polymer and lecithin combination enhances the adsorption of vaccine antigen onto mucosal surfaces. Further, the lecithin composition enhances absorption (Swenson, E S and W J Curatolo, © Means to Enhance Penetration (2) Intestinal permeability enhancement for proteins, peptides and other polar drugs: mechanisms and potential toxicity. Advanced Drug Delivery Reviews. 1992. 8:39-92) that helps bring the antigen in contact with the underlying lymphoid tissue.

The adjuvant composition of this invention makes it possible to vaccinate via a mucosal surface, such as oral cavity, gut, nasal, rectal, or vaginal surfaces. The vaccine may be administered by pill or tablet form, a paste form or in fluid form using a dropper or needleless syringe. This adjuvant composition allows a method of vaccination via food and/or water. The composition can be used traditionally as an injectable as well.

In accordance with the invention, there is provided a method for preparing an adjuvant composition comprising: hydrating lecithin and a polymer in saline or water; and mixing the lecithin and polymer to form an adjuvant.

Preferably, the lecithin and the polymer are mixed by placing the lecithin and the polymer in a blender.

Advantageously, the lecithin and the polymer are mixed in the presence of surfactants.

Preferably, the method further includes the step of microwaving or autoclaving the adjuvant.

In a preferred implementation, from about 0.001-10% by weight dry lecithin and from about 0.001-10% by weight polymer are hydrated. In this implementation, the method preferably further includes the step of adding an antigen. Advantageously, the antigen is added during the hydration step. In another advantageous embodiment, the antigen is added to the adjuvant.

Preferably, the lecithin and the polymer are mixed in the presence of an oil.

The lecithin and the polymer are preferably mixed by placing the lecithin and the polymer in a microfluidizer.

Further features and advantages of the present invention will be set forth in, or apparent from, the detailed description of preferred embodiments thereof which follows.

DETAILED DESCRIPTION OF THE PREFERRED EMBODIMENT

The present invention concerns a vaccine adjuvant which, when admixed with an antigen or hapten and administered into a human or animal, will induce a more intense immune response to the antigen than when the antigen is administered alone. The present invention also concerns vaccines comprising an antigen or group of antigens and a novel adjuvant herein described which comprises a combination of lecithin and a polymer, which is preferably an acrylic polymer. As will appear, the present invention specifically concerns methods of making and using the foregoing adjuvants and vaccines.

The present invention offers the advantage of allowing application of a vaccine directly to a mucosal surface. In doing so, the vaccine stimulates a protective immune response which helps prevent interference from circulating maternal antibodies that may be present in a newborn or infant, for example.

"Antigen" is herein defined as a compound which, when introduced into an animal or a human, will result in the formation of antibodies and cell-mediated immunity.

"Adjuvant" is herein defined as a compound or compounds that, when used in combination with specific vaccine antigens in formulations, augment or otherwise alter or modify the resultant immune responses.

"Vaccine" is herein defined as a composition of antigenic moieties, usually consisting of modified-live (attenuated) or inactivated infectious agents, or some part of the infectious agents, that is administered, most often with an adjuvant, into the body to produce active immunity.

The antigen for use in this invention may be any desired antigen falling within the definition set forth above. Antigens are commercially available or one of skill in the art is capable of producing them. The antigenic moiety making up the vaccine can be either a modified-live or killed microorganism, or a natural product purified from a microorganism or other cell including, but not limited to, tumor cells, a synthetic product, a genetically engineered protein, peptide, polysaccharide or similar product, or an allergen. The antigenic moiety can also be a subunit of a protein, peptide, polysaccharide or similar product. The antigen may also be the genetic antigens, i.e., the DNA or RNA that engenders an immune response. Representative of the antigens that can be used according to the present invention include, but are not limited to, natural, recombinant or synthetic products derived from viruses, bacteria, fungi, parasites and other infectious agents in addition to autoimmune diseases, hormones, or tumor antigens which might be used in prophylactic or therapeutic vaccines and allergens. The viral or bacterial products can be components which the organism produced by enzymatic cleavage or can be components of the organism that were produced by recombinant DNA techniques that are well known to those of ordinary skill in the art. Because of the nature of the invention and its mode of delivery it is very conceivable that the invention would also function as a delivery system for drugs, such as hormones, antibiotics and antivirals.

The lecithin for use in this invention is any lecithin or, for instance, lecithin lipoidal material, such as phosphotidylcholine, that can be used to form liposomes. Phospholipids, lysophospholipids, glycolipids and neutral lipids comprise the typical composition of lecithin. Lecithins are molecules that, when completely hydrolyzed, yield two molecules of fatty acid, and one molecule each of glycerol, phosphoric acid, and a basic nitrogenous compound, which is usually choline. The fatty acids obtained from lecithins on hydrolysis are usually, but not limited to, oleic, palmitic, and stearic acids. The phosphoric acid may be attached to the glycerol in either an $\alpha$- or the $\beta$-position, forming $\alpha$-glycerophosphoric acid or $\beta$-glycerophosphoric acid, respectively, and producing the corresponding series of lecithins which are known as $\alpha$- and $\beta$-lecithins.

Commercial lecithin is obtained by extraction processes from egg yolk, brain tissue, or soybeans. Ovolecithin (vitelin) from eggs and vegilecithin from soybeans, as well as purified lecithin from calf's brains have been used as emulsifiers, antioxidants, and stabilizers in foods and pharmaceutical preparations. Commercial lecithin may be obtained from a variety of sources, for example Central Soya (Fort Wayne, Ind.). One of ordinary skill in the art would be able to determine an appropriate lecithin for a desired application.

The polymer is preferably an acrylic polymer, which is any polymer or copolymer that contains an acrylic moiety. Examples of suitable acrylic polymers include, but are not limited to polyacrylic acid, methacrylic acid, methacrylate, acrylamide, acrylate, acryinitrile, and alkyl-esters of poly acrylic acid. Examples of acrylic copolymers are poly (acrylamide-co butyl, methacrylate), acrylic-methacrylic acid, acrylic-acrylamide and poly (methacrylate). Examples of commercially available acrylic polymers include, Carbopol (B.F. Goodrich Co., Cleveland, Ohio), Carboset, (B.F. Goodrich Co., Cleveland, Ohio), Neocryl (Avecia, Inc., Wilmington, Del.), and Eudragit (Rohm Tech, Inc., Malden, Mass.).

Certain acrylic polymers, such as Carbopol and Eudragit, may benefit from the inclusion of a cross linker, such as a polyalkenyl polyether or an alkyl sucrose, which is effective in binding the polymers. Both Carbopol and Eudragit are available in commercial formulations that include polyalkenyl polyether or alkyl sucrose cross linkers. The most preferred acrylic polymer for use in this invention is polyacrylic acid (Carbopol), with or without a polyalkenyl polyether cross linker. One of ordinary skill in the art would be able to determine an appropriate acrylic polymer for a desired application.

Examples of non-acrylic polymers that are suitable are polyvinyl acetate phthalate, cellulose acetate phthalate, methylcellulose, polyethylene glycol, polyvinyl alcohol, and polyoxyethylene The method of manufacturing the adjuvant of this invention first involves hydrating the lecithin and polymer by suspending from about 0.0001-10% by weight/volume dry lecithin and from about 0.0001-10% by weight polymer in saline or water. The preferred concentrations of lecithin and polymer are 0.001-1.0% each by weight/volume. The two components may be mixed together using conventional methods, such as, for example, a Waring Blender, emulsification equipment or a microfluidizer. Surfactants (emulsifiers) may be added to aid in the mixing or emulsification of the lecithin and polymer. Suitable synthetic detergents are well known to those of ordinary skill in the art. Examples of appropriate surfactants include polyoxyethylene sorbitan monooleate, sorbitan monolaurate, sodium stearate, non-ionic ether-linked surfactants such as Laureth®4 and Laureth®23, alkyl sulfate surfactants, alkyl alkoxylated sulfate surfactants, alkylbenzenesulphonates, alkanesulphonates, olefinsulphonates, sulphonated polycarboxylic acids, alkyl glycerol sulfonates, fatty acyl glycerol sulfonates, fatty oleyl glycerol sulfates, alkyl phenol ethylene oxide ether sulfates, paraffin sulfonates, alkyl phosphates, isothionates such as the acyl isothionates, N-acyl taurates, fatty acid amides of methyl tauride, alkyl succinamates and sulfosuccinates, mono- and diesters of sulfosuccinate, N-acyl sarcosinates, sulfates of alkylpolysaccharides, branched primary alkyl sulfates, alkyl polyethoxy carboxylates, and fatty acids esterified with isethionic acid and neutralized with sodium hydroxide. Further examples are given in *Surface Active Agents and Detergents* (Vol. I and II by Schwartz, Perry and Berch), the disclosure of which is expressly incorporated herein by reference. Suitable nonionic detergent surfactants are generally disclosed in U.S. Pat. No. 3,929,678, Laughlin et al., issued Dec. 30, 1975, at column 13, line 14 through column 16, line 6, incorporated herein by reference. If included, the emulsifier should be added in a concentration ranging from about 0.001-0.05% by volume of the mixture.

Although the invention itself has adjuvant properties, it may also be used in combination with other adjuvants such as, but not limited to, saponins, fractions of saponins, synthesized components of saponins, ISCOMS, muramyl dipeptide and analogues, pluronic polyols, trehalose dimycolate, amine containing compounds, cytokines and lipopolysaccharide derivatives. The addition of another adjuvant may aid in the stimulation of a mucosal immune response. If included, additional adjuvants may be present in a concentration of up to about 10% by weight of the composition, with less than about 1% by weight being preferred.

The invention may also include one or more probiotics. Probiotics are bacteria or microorganisms that are beneficial to the health of the individual or animal. Examples of commonly used probiotics include, but are not limited to, various beneficial strains of *Lactobacillus, Bifidobacterium, Streptococcus*, etc. If present, each of the organisms should be administered in a concentration ranging from about $10^3$ to $10^8$ CFU each.

In addition to all of the above, as is well understood by those skilled in the art, other minors can be employed to make the basic composition more pharmaceutically and/or cosmetically elegant. For example, dyes can be added at very minor levels as can diluents such as alcohol, buffers, stabilizers, wetting agents, dissolving agents, colors, etc. With the exception of diluents such as alcohols which are used at higher levels, the levels of these minors are generally not more than 0.001% to 1.0% by weight.

If desired, the adjuvant components may be sterilized by autoclaving prior to the hydration step. It has also been found that autoclaving and/or microwaving the components may improve their suspending ability. The vaccine antigen may be added after formation of the adjuvant, or at the time the time of hydration of the adjuvant components. If in tablet form, the antigen may be mixed with dry components of the adjuvant invention along with other excipients necessary for tablet formation. Examples of appropriate types of vaccine antigens include killed or attenuated bacterial, viral, parasitic, or sub-units of these organisms, or genomic vaccine antigens, for example, DNA.

The relative concentration of the components, including the antigen, may be determined by testing the formulations in animals starting with a low dose of the formulation and then increasing the dosage while monitoring the immune response. The following considerations should be made when determining an optimal dose, e.g., breed, age, size and the presence or absence of interfering maternal antibodies.

A concentration of an attenuated viral vaccine will comprise about $10^3$ to $10^9$ $TCID_{50}$ per animal. Preferable the amount will be from about $10^4$ to $10^7$ $TCID_{50}$ per animal. The concentration of killed antigen or subunit antigen may range from nanogram to milligram quantities of antigen with about 1 microgram to 1 milligram preferred.

When the acrylic polymer and lecithin are combined, a matrix, or net-like structure is formed. The ratio of lecithin to polymer are ratios between 1:1000 and 1000:1. The preferred ratios of lecithin to polymer are ratios between 1:10 and 10 to 1. The relative proportions of lecithin and acrylic polymer may be found to be important to the efficiency of delivery of different antigens, i.e., bacterial, viral, parasitic or sub-units of these organisms. The optimum ratio may be determined by the conventional means of testing the different ratios of lecithin to polymer with the desired antigen in animals.

The adjuvant composition can be used for the delivery of vaccine antigens such as whole killed or attenuated virus, bacteria, or parasite vaccine antigens or sub-unit(s) of such organisms to mucosal surfaces, such as oral cavity, gut, nasal, vaginal and rectal surfaces. Electron microscopic evaluation shows that there exists a physical and/or chemical affinity between lecithin and polymer. This affinity or association appears as a matrix, or net-like structure. Without intending to be bound by any particular theory, it is believed that a structure such as this can function as a means of physically trapping or encapsulating vaccine antigen. Such binding of antigen is further enhanced by the electrical charge and the hydrophilic and hydrophobic properties of lecithin and the acrylic polymers of this invention. To facilitate this, a polymer of different electrical charge may be selected depending on the anionic or cationic properties of the antigen. Likewise a polymer and lecithin of different hydrophobicity may be selected depending on the lipophilic or hydrophilic properties of the antigen.

If necessary or desired, the antigen can be coupled to the lecithin-acrylic polymer matrix with a cross-linker such as glutaraldehyde in a concentration of from about 1 to 50 mM, and preferably about 15 mM. Further, the antigen can be coupled using water-soluble carbodiimide in a concentration ranging from about 0.05-0.5 M, with about 0.1 M being preferred, or a coupling method using a heterofunctional reagent such as N-hydroxysuccinimidyl 3-(2-pyridyldithio) propionate (SPDP) in a concentration ranging from about 0.1-1.0 mM, and preferably about 0.2 mM. Other appropriate coupling agents include mixed anhydride and bisdiazotized benzidene. The cross-linker is used to improve the binding affinities of the components of the adjuvant composition, for example, where the components are not electrically attracted to each other.

The strong mucoadhesive and adsorptive properties of the acrylic acid/lecithin combination also make it an excellent mechanism to aid in the adsorption of vaccine antigen onto mucosal surfaces. The adjuvant delivery system's absorption enhancement properties helps bring the vaccine antigen in contact with mucosal associated lymphoid tissue. Thus, an immune response is engendered that will aid in the protection of an animal from infections and/or disease process. A robust mucosal immune response is critical since most infectious disease-causing organisms gain entry to the animal at mucosal surfaces. The invention can also be used as an adjuvant for injectable vaccines.

The vaccine comprising the adjuvant is delivered to a mucosal surface by direct application, ingestion through the oral cavity, insertion, injection, and through other conventional means known in the art. Alternatively, the adjuvant may also be administered as a conventional injectable, which is typically either a liquid solutions or suspension. When administered in a food or beverage carrier, the adjuvant/vaccine composition of this invention is generally included in the carrier composition in a concentration ranging from about 0.0001-10% by weight/volume (w/v) in case of a beverage carrier and weight/weight (w/w) in case of a food carrier, with about 0.01-1.0% w/v or w/w respectively, being preferred. When administered in an injectable, the adjuvant/vaccine composition should be present in a concentration ranging from about 0.02-2.0% by weight, with about 0.1-0.5% by weight being preferred.

The adjuvant/vaccine may also be administered in other conventional solid dosage forms, such as in tablets, capsules, granules, troches, and vaginal or rectal suppositories. If administered in a solid dosage form, the adjuvant/vaccine composition should constitute between 0.0001-10% by weight of the dosage form, with about 0.01-1.0% by weight being preferred.

In addition to the active compounds, the pharmaceutical compositions of this invention may contain suitable excipients and auxiliaries which facilitate processing of the active compounds into preparations which can be used pharmaceutically. Oral dosage forms encompass tablets, capsules, and granules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Oral dosage forms may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, including for example, sodium carboxymethyl cellulose, sorbitol and/or dextran. Such compositions may also comprise adjuvants such as preserving, wetting, emulsifying, and dispensing agents. They may also be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

In addition to administration with conventional carriers, active ingredients may be administered by a variety of specialized delivery drug techniques which are known to those of skill in the art, such as portable infusion pumps.

The lecithin/polymer adjuvant of this invention serves multiple functions when it is delivered orally in food and water: 1) it protects the vaccine antigen from degradation by the stomach acid and digestive enzymes; 2) transports the antigen to the mucosal surfaces; 3) facilitates adsorption of the antigen onto the mucosal surfaces; 4) enhances absorption of the antigen; and 5) enhances the immune response to the antigen due to the adjuvant properties of the two components. In the case of delivery to nasal, oral cavity, vaginal and rectal mucosa, the lecithin/acrylic polymer complex functions as a system to deliver and adsorb the antigen to the mucosal surface. Once adsorbed onto the mucosal surface and absorbed, an immune response is engendered.

The combination of polymer and lecithin of this invention unexpectedly provides an improved vaccine delivery system for vaccine antigens. It is apparent that the invention is also an improved delivery system for drugs, such as hormones, antibiotics, probiotics and antivirals. The current invention provides a more simple and efficient method of incorporation of antigen into a delivery system with no, or minimal damage, to vaccine epitopes. The vaccine formulation can be done at low cost and can be easily commercialized as a feed or water additive or as an oral paste or tablet. It is to be understood that these formulations also would be effective in delivering antigen onto other mucosal surfaces, such as nasal, rectal and vaginal surfaces, and would be effective as an adjuvant for an injectable vaccine. In addition, the hydrophobic properties that aid in the adsorption of the adjuvant and vaccine antigen to mucosal surfaces also provides a means of applying to animal feeds, whether it be plant foliage or seeds, both which have a hydrophobic wax surface.

The composition with which the current invention is concerned differs from the prior art in that it comprises a mixture of lecithin and, in a preferred embodiment, an acrylic polymer or copolymer. The invention provides certain advantages over other vaccine delivery systems described in the prior art. It is not prepared under harsh conditions that adversely affect the substance such as the use of organic solvents. It does not require elevated temperatures to manufacture and does not require a stabilization step. The invention provides a simpler method of incorporation of antigen with minimal damage to vaccine epitopes. Using this simpler method of manufacturing results in low cost and ease of commercialization.

The following examples are intended to further illustrate the invention and its preferred embodiments. They are not intended to limit the invention in any manner.

Example 1

Vaccine Plus Adjuvant Effectiveness

An experimental vaccine was made comprising bovine serum albumin Fraction 5 (BSA) (Sigma, St. Louis, Mo.) as a non-living model antigen, lecithin (Centrolex P, Central Soya, Fort Wayne, Ind.) and an acrylic acid polymer resin (Carbopol 934P, (BF Goodrich, Cleveland, Ohio). A second vaccine was made comprising only BSA.

The lecithin and acrylic polymer were suspended together in 150 milliliters (ml) phosphate buffered saline (PBS), each at a concentration of 4 milligrams (mg) per milliliter (ml). The components were first dispersed by stirring with a magnetic stir bar and then mixed further in a Waring Blender using an emulsification head. The mixture was then autoclaved to sterilize the adjuvant mixture. Bovine serum albumin was dissolved in PBS at a concentration of 2 mg/ml and filter sterilized. One part lecithin/acrylic polymer adjuvant was then combined with one part of BSA. Merthiolate (0.01%) was added as a preservative. The final concentration of the vaccine components was 2 mg/ml of the lecithin/acrylic polymer and 1 mg/ml of BSA.

CF-1 female mice, approximately 18 grams, from Charles River Laboratories, (Willmington, Mich.), were injected subcutaneously in the groin area with 0.1 ml of vaccine (0.1 mg. of BSA/dose) on days 0 and 21. Mice were bled on day 45, 24 days after the second vaccination. Mice were bled by cutting the brachial artery following euthanasia by cervical dislocation.

Blood serum Immunoglobulin G (IgG) anti-BSA antibody titers were determined by an enzyme linked immunosorbant assay (ELISA). Results are shown in Table 1.

TABLE 1

Results of antibody titers

| Adjuvant Group | Number Of Mice | Reciprocal of Geometric Mean Titer |
| --- | --- | --- |
| None | 8 | 51,200 |
| Lecithin/Acrylic Polymer | 8 | 157,916 |

Results show that the adjuvant comprising a combination of lecithin and acrylic polymer does indeed enhance the immune response to an antigen.

Example 2

Comparison of Individual Vaccine Adjuvants Administered Orally

Experimental vaccines, for delivery by the oral route, were prepared in PBS. The vaccines comprised the antigen, BSA Fraction 5, at a concentration of 400 micrograms (µg) per ml. Vaccine 1 contained no adjuvant only BSA. Vaccine 2 was comprised of BSA mixed with 3 mg/ml of lecithin, Centrolex P. Vaccine 3 was comprised of BSA mixed with 3 mg/ml of the acrylic polymer, Carbopol 934P. Vaccine 4 was comprised of BSA mixed with 3 mg/ml of lecithin (Centrolex P) and 3 mg/ml of acrylic polymer (Carbopol 934P). Mixing was first done with a laboratory bench top magnetic stir bar and then in a Waring blender using an emulsification head. Lactobacillus culture was added to all vaccines just prior to vaccination. The final concentration of Lactobacillus was 0.01 µg/ml of vaccine. On days 0, 4, 29 and 33 the groups of CF-1 female mice from Charles-River Laboratories and weighing approximately 18 grams, were administered 0.5 ml of vaccine orally by feeding needle. On day 53, 20 days post fourth vaccination, mice were euthanized and bled by the brachial artery. End-point anti-BSA serum IgG antibody titers were determined by ELISA. A 1/100 starting dilution of serum was used due to non-specific background color development at dilutions less than 1/100 Results are recorded in Table 2:

TABLE 2

Effect of adjuvant composition on the anti-BSA antibody response

| Adjuvant Composition | No. of Mice With Titer >/= 1/100 (%) | Reciprocal of Geometric Mean of Mice With Titers |
| --- | --- | --- |
| None | 3/9 (33) | 158 |
| Lecithin | 4/6 (67) | 141 |
| Acrylic Polymer | 6/9 (67) | 8,063 |
| Lecithin and Acrylic Polymer | 6/9 (67) | 45,614 |

Anti-BSA IgG antibody titers were over five times higher when a combination of lecithin and acrylic polymer was used as adjuvant than when acrylic polymer was used alone and 323 times higher than when lecithin was used alone. This demonstrates that the combination of lecithin and acrylic polymer is far more effective at delivering the antigen orally to the mucosal surface for uptake by lymphoid tissue than either lecithin or acrylic polymer alone. Although, not all of the mice showed a serum anti-BSA IgG antibody response the results clearly show a synergistic adjuvant effect of lecithin combined with the acrylic polymer. However, the mice that did not seroconvert may have had a secretory IgA antibody response. Indeed, oral vaccination, and mucosal vaccination in general, stimulates IgA secreting cells at mucosal surfaces.

Example 3

Second Test of Lecithin/Polymer Adjuvant by the Oral Route

Two vaccines were prepared in PBS that comprised the antigen, BSA Fraction 5, at a concentration of 400 ug per ml. One vaccine contained no adjuvant only BSA. The other vaccine was comprised of BSA adjuvanted with 3 mg/ml of lecithin (Centrolex P and 3 mg/ml of acrylic polymer (Carbopol 934P). The vaccine was assembled as described in Example 2. On days 0, 4, 27 and 31 groups of CF-1 female mice from Charles-River Laboratories and weighing approximately 18 grams, were administered 0.5 ml of vaccine orally by feeding needle. On day 52, 21 days post vaccination, mice were euthanized and bled by the brachial artery. End-point anti-BSA serum IgG antibody titers were determined by ELISA. A 1/100 starting dilution of serum was used due to non-specific background color development at dilutions less than 1/100. Results are recorded in Table 3:

TABLE 3

Comparative results of adjuvant versus control

| Adjuvant Composition | No. of Mice with Titer >/= 1/100 (%) | Reciprocal of Geometric Mean of Mice with Titers |
|---|---|---|
| None | 1/12 (8) | 100 |
| Lecithin and Acrylic Polymer | 9/11 (82) | 18,812 |

This study again demonstrates that the combination of lecithin and acrylic polymer is effective in delivering antigen to oral mucosal surfaces.

In a separate study, 4/10 mice that received this same vaccine, had a geometric mean titer of 1/1,345 six weeks after only a single vaccination. This demonstrates the potential of the adjuvant composition, when once optimized, to engender an immune response of long duration.

Example 4

Administration of Vaccine Intranasally

Two experimental vaccines for delivery by the intranasal route were prepared in PBS comprising the antigen, BSA, at a concentration of 500 µg/ml. One vaccine was comprised of BSA alone. The second vaccine was comprised of BSA adjuvanted with a combination of 3 mg/ml of lecithin (Centrolex P) and 3 mg/ml of the acrylic polymer, Carbopol 934P. The lecithin and acrylic polymer were first mixed with a laboratory bench top magnetic stir bar and then in a Waring blender using an emulsification head. BSA was then added and mixed again using the emulsification head. Mice were vaccinated on days 0 and 20. Forty µl containing 20 µg of BSA antigen were placed on the nose while the mouth was held shut. The vaccine entered the nose when the mouse inhaled. On day 41, 21 days post second vaccination, the mice were euthanized and bled by cutting the brachial artery. Anti-BSA antibody titers were determined by ELISA. The starting dilution of serum was at 1/100 due to non-specific background color development at lower dilutions. Results are shown in Table 4:

TABLE 4

Comparative results of adjuvant vs. control

| Adjuvant Composition | No. of Mice with Titer >/= 100 (%) | Reciprocal of Geometric Mean of Mice with Titers |
|---|---|---|
| None | 0/11 (0%) | 0 |
| Lecithin and Acrylic Polymer | 7/12 (58%) | 269 |

None of the mice (0/11) vaccinated with BSA alone seroconverted. The BSA antigen alone, when administered intranasally, failed to stimulate a serum antibody response in any of the mice. In contrast, 7 of 12 mice, or 58%, developed serum anti-BSA IgG antibody titers as high as 1/3200 following intranasal vaccination with BSA in combination with the invention comprised of lecithin and acrylic polymer. The fact that not all mice seroconverted suggests that not enough, or perhaps none of the vaccine was inhaled by those mice that did not have an antibody titer greater than 1/100. Indeed, some, perhaps most, of the vaccine was observed to run off the nose or was blown off the nose when the mouse exhaled. Still, the results of this study show that the invention, comprised of lecithin and acrylic polymer, functions effectively as an adjuvant for the intranasal delivery of a vaccine antigen.

Example 5

Use of Adjuvant with Vaccine in Swine

The adjuvant invention comprising a combination of 2 mg/ml of lecithin (Centrolex P) and 2 mg/ml of acrylic polymer (Carbopol 934P) was used as a diluent for modified-live pseudorabies virus (ML-PRV) for swine. This adjuvant diluent and a control diluent consisting of sterile water were used to rehydrate lyophilized (ML-PRV). The ML-PRV was rehydrated immediately prior to vaccination. Groups of 10 weaned piglets, 6 weeks of age, were vaccinated on days 0 and 21. Blood serum was collected on days −2, 20, 28 and 48 for serological testing for anti-PRV serum neutralizing antibodies. The anti-PRV antibody responses of piglets in the different vaccine groups are shown in Table 4.

TABLE 5

Results in pigs

| Adjuvant Diluent | Geometric Mean Virus Neutralizing Antibody Titer on Days Post First Vaccination | | | |
|---|---|---|---|---|
| | Day 2 | Day 20 | Day 28 | Day 48 |
| Non-Vaccinated Control | 0 | 0 | 0 | 0 |
| Water | 0 | 4 | 34 | 21 |
| Lecithin/ Acrylic Polymer | 0 | 6 | 69 | 52 |

This study showed that the invention comprising a lecithin and acrylic polymer combination functions as an adjuvant for a ML-virus vaccine adjuvant, in this case swine ML Pseudorabies vaccine virus. The virus neutralizing anti-PRV antibody titer to ML-PRV, which by itself is a very good antigen without an adjuvant and is used commercially without an adjuvant, was over twice as high when the lecithin/acrylic polymer was used instead of water.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method for preparing a vaccine comprising:
   combining a dry lecithin with an acrylic polymer at a ratio of 1:10 to 10:1 by weight;
   suspending the combined lecithin and acrylic polymer in saline or water; and
   mixing the lecithin and polymer suspension to form a matrix or netlike structure;
   wherein the vaccine is prepared without the use of an organic solvent;
   wherein an antigen is added before or after suspension of the dry lecithin and acrylic polymer combination such that the antigen is embedded in the matrix or netlike structure to form the vaccine, and wherein the vaccine is used to elicit an immune response against an infectious agent, cancer, hormone, or autoimmune disease.

2. The method of claim 1 wherein the antigen is added before suspension of the dry lecithin and acrylic polymer combination.

3. The method of claim 1, wherein the antigen is selected from the group consisting of modified live microorganism, killed microorganism, natural product from a tumor cell, synthetic product, genetically engineered protein, peptide, genetically engineered peptide, genetically engineered polysaccharide, DNA that engenders an immune response, RNA that engenders an immune response, viral products, bacterial products, fungal products, parasite products, hormones, autoimmune disease products, tumor antigens, and combinations thereof.

4. The method of claim 1, wherein the antigen is added after suspension of the dry lecithin and acrylic polymer combination.

5. The method of claim 1, wherein the dry lecithin and acrylic polymer are combined at a ratio of 1:1 by weight.

6. The method of claim 1, wherein the step of mixing the lecithin and polymer suspension to form a matrix or netlike structure comprises emulsifying the lecithin and polymer suspension.

7. A method for preparing an adjuvant comprising:
combining a dry lecithin with an acrylic polymer at a ratio of 1:10 to 10:1 by weight;
suspending the combined lecithin and acrylic polymer in saline or water; and
mixing the lecithin and acrylic polymer suspension to form an adjuvant, wherein the adjuvant has a matrix or netlike structure;
wherein the adjuvant is prepared in the absence of an organic solvent; and
wherein an antigen, a drug, an antibiotic, an antiviral, or probiotic is added before or after suspension of the dry lecithin and acrylic polymer combination and the antigen, drug, antibiotic, antiviral, or probiotic is embedded in the adjuvant.

8. The method of claim 7, wherein the antigen is selected from the group consisting of modified live microorganism, killed microorganism, natural product from a tumor cell, synthetic product, genetically engineered protein, peptide, genetically engineered peptide, genetically engineered polysaccharide, DNA that engenders an immune response, RNA that engenders an immune response, viral products, bacterial products, fungal products, parasite products, hormones, autoimmune disease products, tumor antigens, and combinations thereof.

9. The method of claim 7, wherein the antigen is added after suspension of the dry lecithin and acrylic polymer combination.

10. The method of claim 7, wherein the dry lecithin and acrylic polymer are combined at a ratio of 1:1 by weight.

11. The method of claim 7, wherein the step of mixing the lecithin and polymer suspension to form a matrix or netlike structure comprises emulsifying the lecithin and polymer suspension.

12. A method for preparing a vaccine comprising:
combining a dry lecithin with an acrylic polymer at a ratio of 1:10 to 10:1 by weight;
suspending the combined lecithin and acrylic polymer in saline or water; and
emulsifying the lecithin and polymer suspension to form a matrix or netlike structure;
wherein an antigen is added before or after suspension of the dry lecithin and acrylic polymer combination such that the antigen is embedded in the matrix or netlike structure to form the vaccine,
wherein the vaccine is used to elicit an immune response against an infectious agent, cancer, hormone, or autoimmune disease, and
wherein the vaccine is prepared in the absence of an organic solvent.

13. A method for preparing a vaccine comprising:
combining a dry lecithin with an acrylic polymer at a ratio of 1:10 to 10:1 by weight;
suspending the combined lecithin and acrylic polymer in saline or water; and
mixing the lecithin and polymer suspension to form an emulsion of the lecithin and polymer;
wherein an antigen is added before or after suspension of the dry lecithin and acrylic polymer combination such that the antigen is embedded in the emulsion to form the vaccine,
wherein the vaccine is used to elicit an immune response against an infectious agent, cancer, hormone, or autoimmune disease, and
wherein the vaccine is prepared in the absence of an organic solvent.

* * * * *